US011160730B2

(12) United States Patent
Townley (10) Patent No.: US 11,160,730 B2
(45) Date of Patent: Nov. 2, 2021

(54) SMART MEDICATION DISPENSING SYSTEM AND METHOD

(71) Applicant: Rightis Technology, LLC, Minneapolis, MN (US)

(72) Inventor: Patrick Townley, Minneapolis, MN (US)

(73) Assignee: Rightis Technology, LLC, Minneapolis, MN (US)

( * ) Notice: Subject to any disclaimer, the term of this patent is extended or adjusted under 35 U.S.C. 154(b) by 94 days.

(21) Appl. No.: 16/438,158

(22) Filed: Jun. 11, 2019

(65) Prior Publication Data

US 2019/0374436 A1 Dec. 12, 2019

Related U.S. Application Data

(60) Provisional application No. 62/683,459, filed on Jun. 11, 2018, provisional application No. 62/723,465, filed on Aug. 27, 2018, provisional application No. 62/776,088, filed on Dec. 6, 2018.

(51) Int. Cl.
*A61J 7/00* (2006.01)
*A61J 7/04* (2006.01)

(52) U.S. Cl.
CPC .............. *A61J 7/0076* (2013.01); *A61J 7/04* (2013.01)

(58) Field of Classification Search
CPC combination set(s) only.
See application file for complete search history.

(56) References Cited

U.S. PATENT DOCUMENTS

| 5,597,072 A * | 1/1997 | Lieberman ................ A61J 1/03 206/531 |
| 5,710,551 A | 1/1998 | Ridgeway |
| 6,394,306 B1 | 5/2002 | Pawlo et al. |
| 6,411,567 B1 | 6/2002 | Niemiec et al. |

(Continued)

FOREIGN PATENT DOCUMENTS

| WO | WO2000017799 A1 | 3/2000 |
| WO | WO2000032097 A1 | 6/2000 |

(Continued)

OTHER PUBLICATIONS

The International Search Report and Written Opinion rendered by the International Searching Authority for PCT/US2019/036599, dated Aug. 27, 2019, 11 pages.

(Continued)

*Primary Examiner* — Kyle O Logan
(74) *Attorney, Agent, or Firm* — Taft Stettinius & Hollister LLP; Gerald E. Helget (57) ABSTRACT

A personalized medication dispensing system provides a practical, cost effective, and convenient way to optimize and individualize medical care. The system can be linked to the patient, doctors, insurers, pharmacies, and the like, via network communication protocols and techniques. The system can include a medication reservoir section and a medication dispensing section. The medication reservoir section includes one or more rotatable medication reservoirs. The system includes software configured to process and facilitate dispensing, treatments, data, monitoring, notifications, and trials, including treatment of specific medical conditions.

14 Claims, 8 Drawing Sheets

(56) References Cited

U.S. PATENT DOCUMENTS

| | | | |
|---|---|---|---|
| 6,574,166 | B2 | 6/2003 | Niemiec |
| 7,048,141 | B2 | 5/2006 | Abdulhay et al. |
| 7,909,207 | B2 | 3/2011 | Handfield et al. |
| 8,014,232 | B2 | 9/2011 | Niemiec et al. |
| 8,193,918 | B1 | 6/2012 | Shavelsky et al. |
| 8,417,378 | B2 | 4/2013 | Joslyn |
| 8,744,620 | B2 | 6/2014 | Shavelsky et al. |
| 8,977,390 | B2 | 3/2015 | Jefferies et al. |
| 9,211,233 | B2 | 12/2015 | Shavelsky et al. |
| 9,358,499 | B2 | 6/2016 | Akdogan et al. |
| 9,358,500 | B2 | 6/2016 | Adkogan et al. |
| 9,463,412 | B2 | 10/2016 | Akdogan et al. |
| 9,489,493 | B2 | 11/2016 | Jefferies et al. |
| 9,501,887 | B2 | 11/2016 | Berg et al. |
| 9,533,300 | B2 | 1/2017 | Richter |
| 9,550,619 | B2 | 1/2017 | Park, IV |
| 9,731,853 | B2 | 8/2017 | Akdogan et al. |
| 9,836,583 | B2 | 12/2017 | Garcia et al. |
| 10,102,706 | B2 | 10/2018 | Jefferies et al. |
| 10,106,283 | B2 | 10/2018 | Akdogan et al. |
| 10,173,830 | B2 | 1/2019 | 'T Lam et al. |
| 10,360,751 | B2 | 7/2019 | Berg et al. |
| 10,555,874 | B2 | 2/2020 | Feng et al. |
| 10,685,091 | B1 | 6/2020 | Park, IV et al. |
| 10,723,541 | B2 | 7/2020 | Akdogan et al. |
| 10,730,687 | B2 | 8/2020 | MacVittie et al. |
| 10,751,239 | B2 | 8/2020 | Volek et al. |
| 10,789,803 | B2 | 9/2020 | Jefferies et al. |
| 2005/0076969 | A1* | 4/2005 | Tahil ................ A61J 3/075 141/165 |
| 2006/0259188 | A1* | 11/2006 | Berg ................ G07F 11/54 700/231 |
| 2009/0295575 | A1* | 12/2009 | Kennedy ........... G07F 9/026 340/540 |
| 2010/0076595 | A1* | 3/2010 | Nguyen ............ A61J 7/0481 700/232 |
| 2010/0096399 | A1* | 4/2010 | Ratnakar ........... G07F 11/44 221/1 |
| 2011/0278319 | A1* | 11/2011 | Knoth ............... B65B 5/103 221/1 |
| 2013/0035785 | A1* | 2/2013 | MacVittie .......... A61J 7/0076 700/231 |
| 2014/0353328 | A1* | 12/2014 | Makhalfeh ......... A61J 7/04 221/15 |
| 2015/0039124 | A1* | 2/2015 | Mistovich .......... G07F 11/16 700/237 |
| 2015/0251839 | A1* | 9/2015 | Denny ............... G16H 20/10 340/686.6 |
| 2015/0272830 | A1* | 10/2015 | Iordanov ............ G06F 19/00 221/1 |
| 2016/0039553 | A1 | 2/2016 | Akdogan et al. |
| 2016/0107820 | A1 | 4/2016 | Macvittie et al. |
| 2016/0151246 | A1* | 6/2016 | Sotelo .............. A61J 7/04 221/1 |
| 2017/0239144 | A1* | 8/2017 | Terhune ............ B65D 83/0463 |

FOREIGN PATENT DOCUMENTS

| | | |
|---|---|---|
| WO | WO2000072452 A2 | 11/2000 |
| WO | WO2013025520 A2 | 2/2013 |
| WO | WO2020092338 A1 | 5/2020 |

OTHER PUBLICATIONS

Salama, Diaa et al., "Smart drugs: Improving healthcare using Smart Pill Box for Medicine Reminder and Monitoring System," Nov. 29, 2018, 14 pages.

Pak, JuGeon et al., "Construction of a Smart Medication Dispenser with High Degree of Scalability and Remote Manageability," Jun. 2, 2012, 11 pages.

* cited by examiner

SMART MEDICATION DISPENSING SYSTEM AND METHOD

PRIORITY

This application claims priority to and the benefit of U.S. Provisional Patent Application No. 62/683,459, filed Jun. 11, 2018, U.S. Provisional Patent Application No. 62/723,465, filed Aug. 27, 2018, and U.S. Provisional Patent Application No. 62/776,088, filed Dec. 6, 2018, with each of the identified applications and disclosures incorporated fully herein by reference.

FIELD

The present invention relates generally to dispensing and, more particularly, to a precision medication dispensing system and method configured to optimize and individualize medical care.

BACKGROUND

Doctors and other clinicians face several treatment obstacles when optimizing medical care for individual patients, including choosing the best medication, the optimal dose of the medication, determining and encouraging compliance, measuring the effect of treatment, and maintaining communication with their patients.

Doctors frequently are unable to identify the best treatment for their patients. Even when doctors follow guidelines based on the "best evidence" from medical research, patients often fail to respond to or are sometimes harmed by their medications. This is because medical research focuses on the effect of medications on large populations, research results are measured in the aggregate, and statistical analysis is used to determine if, on average, the medication was beneficial. But even when beneficial on average, many patients within the population will not benefit and some will be harmed by the treatment medication. The large research trials which are the gold standard of medicine fail to account for the fact that each patient is a unique individual with a unique genetic profile. As a result, the large group comparison studies of medical research rarely result in treatments that work ubiquitously for chronic diseases most commonly faced by clinicians.

The answer to this problem can be to conduct separate clinical trials for each patient. These trials, known as N-of-1 trials, have been conducted for years within specialized academic settings and utilize much of the design components of the large population-based clinical trials, including randomization, double blinding, washout and crossover periods, placebo controls, and various techniques of statistical analysis. However, the process is cumbersome, lengthy, and resource intensive. Patients must follow complex instructions about which pills to take and when, all while the nature of the treatment is hidden from them and their doctor. To do this requires extensive resources and a large support staff including nurses, pharmacists, statisticians and others.

The elimination of potential biases in a trial is a major requirement. While bias elimination can be achieved by introducing "blinding" into the study, the requisite physical characteristics and indicia of medications makes this difficult. Pills and other medications have distinct shapes, colors, and sizes, and if a patient is able to easily identify a medication due to these attributes, a potential bias is introduced. A controlled and truly "blind" trial, therefore, means the participants in the trial must not be able to identify specific medications by their physical characteristics. However, it is a costly and cumbersome process to custom manufacture medications in a manner that renders the pills non-distinguishable from other pills. While over-encapsulation can be used to achieve this goal, it is currently an extensive and time-consuming process that is often avoided. For these reasons, N-of-1 trials remain largely under-utilized, and doctors rely instead on a one-size-fits all approach to treatment.

In addition, there is a current problem where clinicians fail to change current pharmacotherapies, either by changing dose or type of medications, when treatment target goals are not achieved. The problem arises in part from the difficulty of measuring the effect of treatments by obtaining timely information from patients, including description of symptoms and biophysical measurements. This, in turn, leads to poor control of diseases and risk factors, and minimizes the chances of helpful and reactive adjustments to patient treatments.

Lastly, pharmacotherapeutic nonadherence is a material problem. Nonadherence occurs when patients do not take the pharmacotherapies prescribed to them or fail to take the medications at specifically prescribed times. This can diminish the impact of medical treatments, and the overall effectiveness of medications being prescribed to an individual patient.

Accordingly, there is a need for new and improved systems and methods to solve the innate issues around ensuring that a particular pharmacotherapy is the right choice for a patient, ensuring that a particular pharmacotherapy dose is right for a patient, ensuring treatment effectiveness, and ensuring that adherence will be promoted.

SUMMARY

Embodiments of the present invention comprise a system including a personalized "countertop" medication control, monitoring, and dispensing device provided with network connectivity (e.g., local network, the Internet, etc.). The device can include a body or housing portion, one or more reservoirs to manage and deliver medications, a dispensing section, and input and output devices, such as a display screen, audio output, and the like. Concealed treatments can be promoted and can include stamped barcodes provided on formed capsules to facilitate identification.

In various embodiments, the system is prefilled with specific medications and the software of the system provides treatment protocols consistent with professional recommendations, published and accepted methodologies, etc.

The system can include a medication reservoir assembly and a dispensing assembly, and may or may not include an over-encapsulation compartment or mechanism. A central drive of the medication reservoir is operatively connected or registered with a mateable motor of the dispensing assembly such that the reservoirs selectively rotate or index on or about the dispensing assembly. The medication reservoirs can be defined as medication pods and the medication reservoir assembly can be disposable and delivered such that the patient can use and discard or dispose of the entire reservoir assembly, or a portion thereof. Rotation of the reservoir assembly resultingly aligns at least one of a plurality of reservoirs and a corresponding bottom outlet of the reservoir assembly with a top inlet of the dispensing assembly such that medication, such as one or more pills or capsules, can drop through the bottom outlet and into the top inlet for dispensing through the dispenser. A portion of the reservoirs can rotate to eject the pills from the pods and into the dispensing assembly.

The system of the present invention dispenses precise doses of medication and can collect data used to measure the effect of the medication, including biophysical measurements (e.g., weight, blood pressure, heart rate, blood glucose level, etc.) and descriptions of symptoms.

In various embodiments of the dispensing system, the medications can be provided in solid, powder, or liquid form and can be contained within separate pods or reservoirs inside of the countertop device. On command, the machine can transfer an exact measured dose of medication from the reservoir into a solution that is dispensed to the patient. In other embodiments, the device uses medications in their original tablet or capsule form and encapsulates the medications when the treatment protocol requires concealment of treatment (blinding). In addition, the medications can be delivered already over-encapsulated and preloaded into a reservoir or dispensing assembly, mechanism, or device.

Many patients fail to benefit or are harmed when clinicians simply prescribe the medications identified in clinical trials as "the best treatment" within a population. For an individual, identifying the best treatment often requires an N-of-1 trial. Without the present invention, however, conducting an N-of-1 trial is extremely resource intensive and cumbersome. The conventionally available processes are not patient-friendly and only a handful of academic intuitions are willing to absorb the cost and commit the resources to this approach.

The medication dispensing system of the present invention is controlled by a software algorithm that can implement an N-of-1 trial protocol, in certain embodiments. The N-of-1 protocol is a scientifically validated manner of comparing the effects in an individual of two treatments. The present invention can use over-encapsulation to make N-of-1 trials practical. Over-encapsulation conceals trade dress and any imprinted identifiers, while maintaining blinding. The pills being compared are hidden inside identical opaque shells. The over-encapsulated pills are visually identical, because the visually distinct pills on the inside are concealed.

Typically, treatment A is administered for a set period of time and its effects are measured. Then, treatment B is administered for the same length of time and its effects are measured. The treatments are blinded (neither patient nor doctor know the drug being dispensed) and the order of treatment is randomized. At the end of the trial, the measured effects of the treatments are analyzed and any difference (or possibly no difference) in treatment effect is revealed.

The N-of-1 protocol allows any two variables to be compared. This could be drug A vs. drug B, drug A vs. placebo, drug A vs. drug combination C, a lower dose of drug A vs. a higher dose of drug A, taking drug A in the morning vs. taking drug A in the evening, and so on. Once the optimal treatment is identified, its ongoing effectiveness is monitored through the present invention's data inputs.

The system can collect, process, and communicate data via wired or wireless (Wi-Fi, Bluetooth, NFC, etc.) connections to peripheral or like devices, including weight scales, blood pressure monitoring devices or cuffs, blood glucose monitors, wearables (Apple Watch, Fitbit, etc.), and the like. Data is also obtained periodically from the patient when they answer (e.g., input) symptom questionnaires or rate the severity of their symptoms. This information can be gathered by an app on a device, such as a mobile device (e.g., smartphone, tablet, etc.), a desktop computer, or other computing devices, or entered directly into the system using its keypad or touch screen inputs. The present invention can be programmed so that when data includes measurements that fall outside of predetermined ranges, like a blood pressure consistently above a desirable level, an alert or notification can be sent to a clinic or clinician. The system can also send automatic refill requests to clinics or pharmacies when medication within the medication reservoirs drop below a certain level.

Several aspects of the dispensing system improve accuracy and safety of treatments. For example, when the device encapsulates medications, or with medications not incapsulated, it labels the capsule or a portion of the reservoirs with a bar code or other indicia that can be used to identify the medication. If the patient fails to take medications as prescribed, or if the patient is running low or has run out of medication, an alert can be sent to the patient, the subject pharmacy, the prescriber of the medication, and the clinician who is treating the patient. Adherence reports can be generated by the system to manage and promote adherence, and insurers can track adherence as well to provide additional incentives for the patient. Further, alerts can be sent to the patient to remind the patient that they need to take their medications, thereby promoting adherence. Each person or entity involved with the treatment, prescribing process, or with an interest in tracking adherence or treatment, can operatively communicate and interact with the dispensing system via one or more network computing systems, such as a cloud computing system.

In addition to providing a clinically practical tool for identifying the best medication and dose for an individual, embodiments of the invention will allow patients to obtain precise dosages of medication. No longer will patients be forced to use the arbitrary dosages contained in pills or capsules. For example, instead of the patient and doctor having to decide between the 50 mg pill or the 100 mg pill, the dispensing system can precisely dispense the optimal dose of medication, even if the optimal dose is 67 mg for that individual.

The above summary is not intended to describe each illustrated embodiment, claimed embodiment or implementation of the invention. The detailed technology and preferred embodiments implemented for the subject invention are described in the following paragraphs accompanying the appended drawings for people skilled in this field to well appreciate the features of the claimed invention. It is understood that the features mentioned hereinbefore and those to be commented on hereinafter may be used not only in the specified combinations, but also in other combinations or in isolation, without departing from the scope of the present invention.

BRIEF DESCRIPTION OF THE DRAWINGS

The invention may be more completely understood in consideration of the following detailed description of various embodiments of the invention in connection with the accompanying drawings, in which.

While the invention is amenable to various modifications and alternative forms, specifics thereof have been shown by way of example in the drawings and will be described in detail. It should be understood, however, that the intention is not to limit the invention to the particular embodiments described. On the contrary, the invention is to cover all modifications, equivalents, and alternatives falling within the spirit and scope of the invention as defined by the appended claims.

DETAILED DESCRIPTION OF THE INVENTION

Referring generally to FIGS. 1-15, a personalized and smart medication dispensing and health information system 100 is provided. A medication reservoir section and a dispensing section can be included to provide a small and complete unit uniquely configured for personal patient usage.

Figure 1:
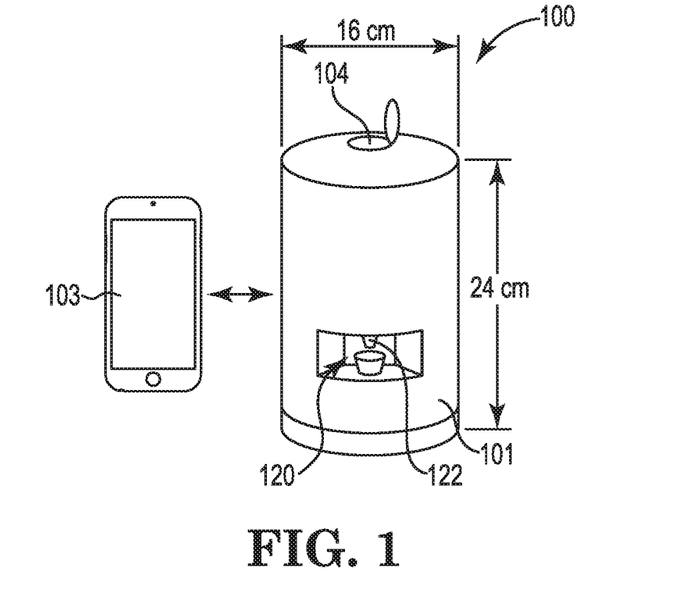
FIGS. 1-6 show exemplary medication dispensing systems, and corresponding sections, assemblies, and components thereof, in accordance with embodiments of the present invention.
Figure 2:
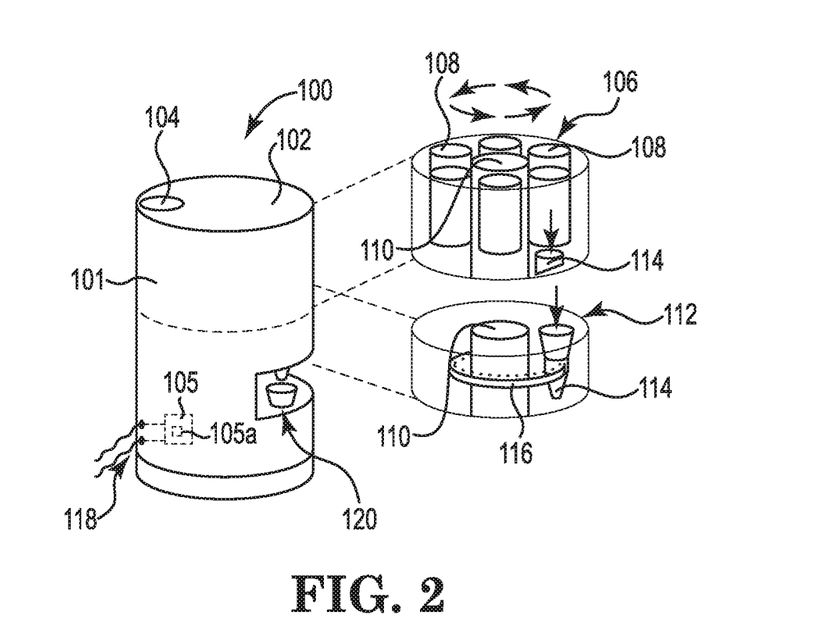
Figures 3, 4:
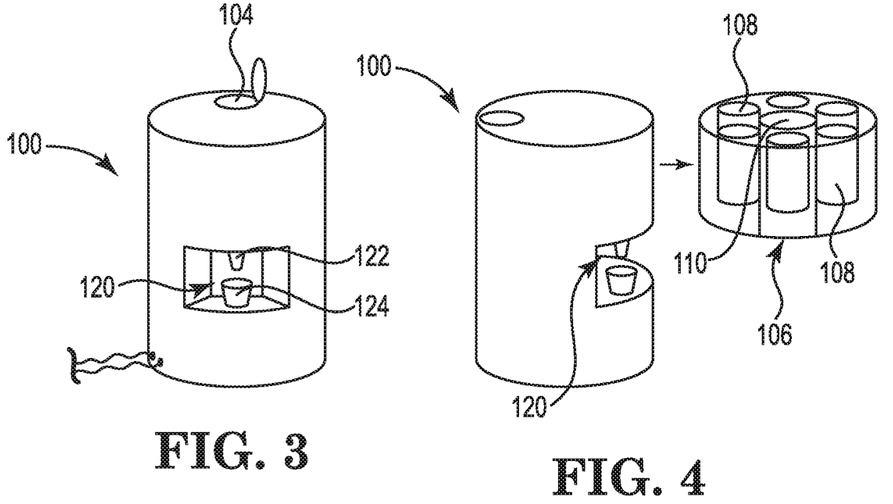
Figure 5:
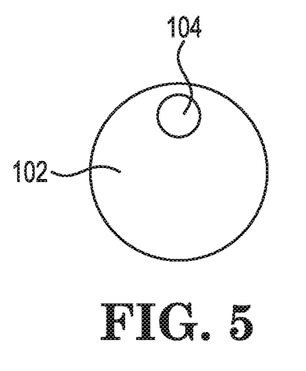
Figure 6:
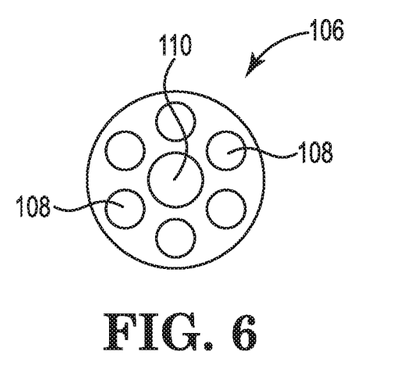
Figures 8, 9, 10, 11:
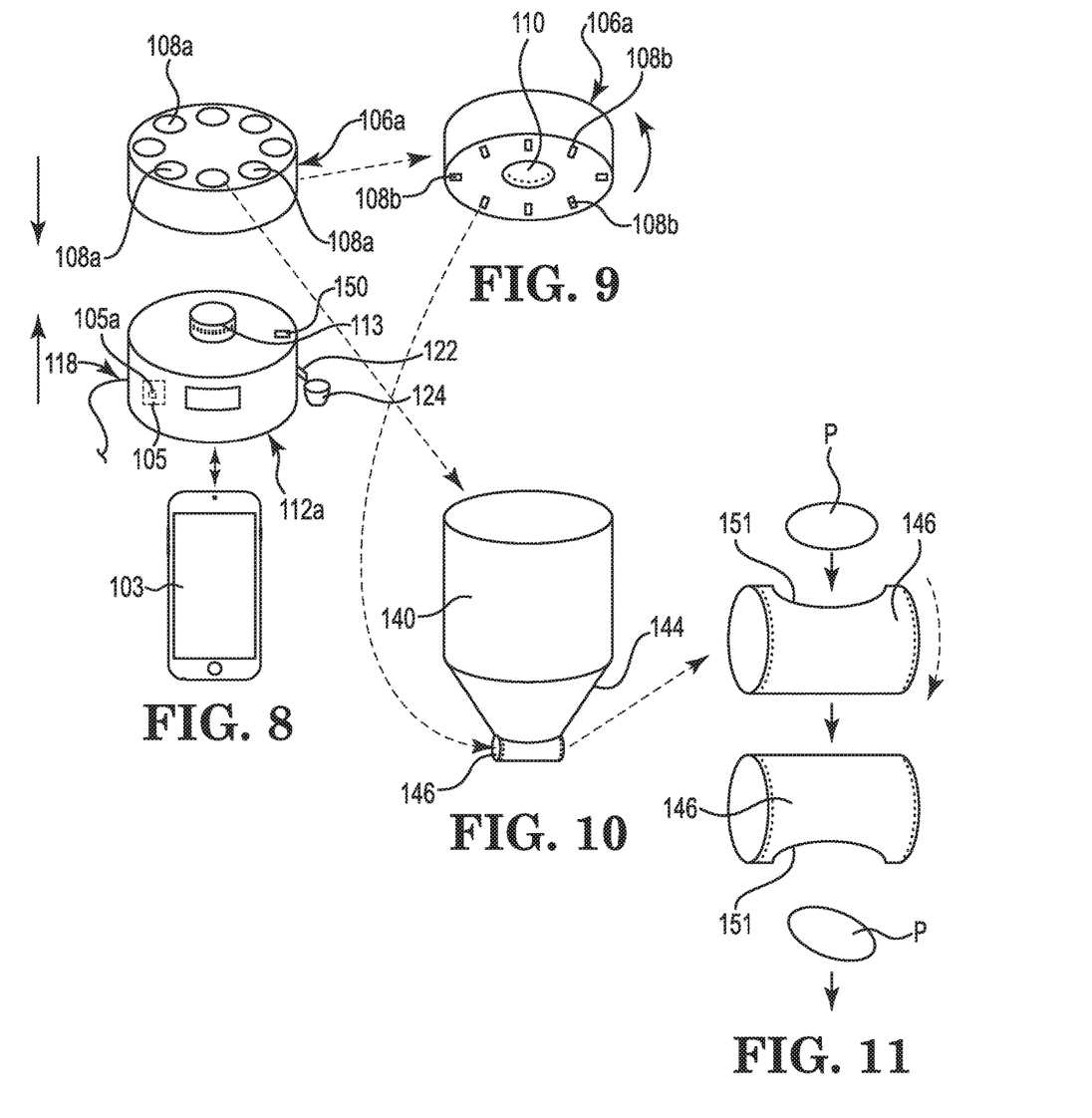
FIGS. 8-9 show a rotatable medication reservoir assembly and a dispensing assembly for a medication dispensing system, in accordance with embodiments of the present invention.
FIGS. 10-11 show a medication reservoir or pod and rotatable dispensing of medication for a medication dispensing system, in accordance with embodiments of the present invention.

Each embodiment of the dispensing system 100 can comprise a controller 105 or like electronic hardware that can include a microprocessor 105a and physical memory coupled to the microprocessor 105a (e.g., FIGS. 2 and 10). One or more of these system components (e.g., controller 105, processor 105a, memory, etc.) can be provided with the dispensing section and/or the reservoir section for embodiments of the system 100. A computer readable program code can be stored in the physical memory (e.g., random access memory, flash memory, or storage drive) of the system. The computer readable program code is configured such that when executed by the processor 105a, the code causes the dispensing device to perform the steps and processing of the invention described herein. A communication, storage, and power section can be provided at section 118 of the system 100. For example, ethernet and USB ports can be included with section 118 and in operative communication with the processor 105a. In addition, the system 100 can include network components to facilitate wired and wireless (e.g., Bluetooth, Wi-Fi, etc.) communication.

Referring to FIGS. 1-6, embodiments of the system 100 can include a main body or housing portion 101. An upper portion of the body 101 can include a medication reservoir section or assembly 106. The reservoir assembly 106 can have a removable lid or top portion 102, which can include a medication load or fill port 104. An output dispensing section 120 is also provided and can include a bottom dispensing assembly 112 for dispensing the medication to a myriad of receiving vessels or devices, such as a cup 124.

The medication reservoir section 106 can include one or more medication reservoirs 108 and a central drive and axis 110. The central drive 110 is operatively connectable and registerable with a motor of the dispensing section 120 such that the reservoirs 108 are capable of selectively rotating about the dispensing section 120. Upon rotation, the reservoirs 108 will individually align with the fill port 104 for receiving medication into one or more of the reservoirs 108, and then moving from a position under the fill port 104 on top of the device to a position above a dispensing and/or encapsulation chamber. The medication within the aligned reservoir 108 is then dispensable through the dispensing assembly 112.

With such embodiments, the reservoirs 108 are large enough for each to contain 90 to 120 pills or capsules. When in the fill position, the top of a reservoir 108 is open and centered beneath the fill hatch 104. Capsules or pills P are easily poured into the reservoir 108 via the hatch 104. After the first aligned reservoir 108 is filled, the group of medication reservoirs 108 then rotates around the axis 110 such that the next empty reservoir 108 moves into the fill position in alignment with the hatch 104. The filling and identification process can be repeated for each included reservoir 108. With other embodiments, the reservoirs 108 are sized and shaped to hold a single pod that contains medication in a solid, liquid or powder form and may not include a fill port.

Before, during, and after the filling process is complete, software within the processor 105a allows the patient's doctor, or other medical personnel, to monitor and control the insertion of medications and how those medications are dispensed. As described further herein, the doctor's instructions can be delivered to the dispensing device via a cloud computing device (e.g., Internet connected), a USB thumb drive, or a medical personnel device in operative communication with the system 100, controller 105, and processor 105a. The provided dispensing data and instructions enable the system 100 to deliver medication in any specified combination, timing, or other pattern. The system software also allows the doctor to personalize or optimize treatment by conducting trials or treatment regimens that require medications to be dispensed according to predetermined protocols. The unique software and medication delivery mechanism gives doctors a practical tool to deliver optimal care when the best treatment is known, and dynamically when the best treatment is not known.

Figure 7:
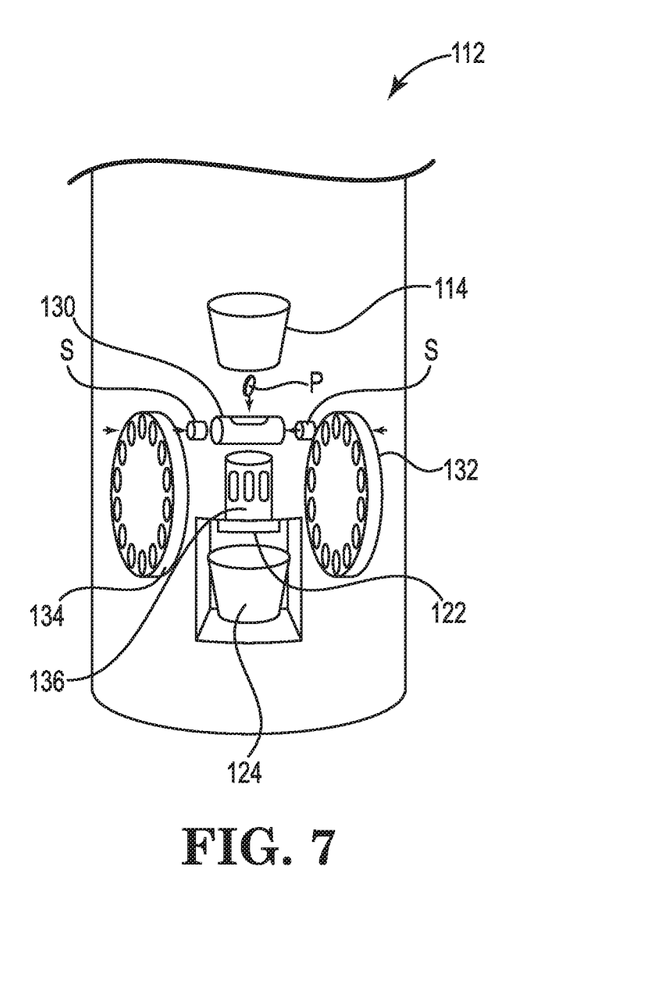
FIG. 7 shows an encapsulation compartment and mechanisms for a medication dispensing system, in accordance with embodiments of the present invention.

Referring to FIG. 7, certain embodiments of the system 100 can include an encapsulation section or chamber within the body 101. Capsules or pills P drop from a medication reservoir 108 into a funneling device 114 that precisely positions the medication within an over-encapsulation compartment or assembly. The compartment can be provided with dispensing assembly 112 or section 120. In various embodiments, the over-encapsulation compartment can be included with the medication reservoir assembly 108 or as a section separate from the dispensing assembly 112 and reservoir assembly 108. Provided in the center of this cylindrical compartment with this embodiment, the medication is then covered by the hollow shells S of a capsule at mechanism 130. The top and bottom shells S are each pushed into opposite ends of the cylinder 130 from revolving cartridges 132, 134. Slots or other constructs on the front of the system allow the cartridges to be inserted and later ejected when empty.

After the medication has been covered, the cylinder 130 rotates, and the medication drops through an opening into a chamber mechanism 136 where the newly formed capsule shells are heat sealed and stamped with a bar code that can be used to identify the medication within the capsule. The medication then drops via device or element 122 and out into the patient's pill or medication cup 124. When over-encapsulation is not necessary, the medications simply funnel down through the middle section 112, bypassing the above-described mechanisms, and the pills, capsules, solution, and the like, are simply dispensed through the output 120 in their original form.

In other embodiments of the system 100, the medication reservoirs 108 are configured as, or include, pods filled with medication that has not been divided or shaped into pills, capsules, or other separate dosing forms. In certain embodiments, the medication within these reservoir pods can be in a liquid, solid, or powder form. In this version of the system 100, an over-encapsulation chamber 112 would not need to be included. Instead, a precision dosing mechanism is included that measures the exact dose of each medication. The medication is then placed into a solution or form that is dispensed to the patient through the output 120.

Referring to FIGS. 8-11, an embodiment of the system 100 comprising a medication reservoir or chamber assembly 106a and a dispensing assembly 112a is shown. The assemblies 106a, 112a can be included with, housed in, or otherwise include any of the devices, mechanisms, housings, structures, body sections, software, and the like disclosed herein for various embodiments. The reservoir assembly 106a can include one or more medication reservoirs 108a and a central drive or axis 110. The medication reservoirs 108a extend through the reservoir assembly 106a to define bottom outlets 108b. The central drive section 110 is operatively connected or registered with a mateable drive element and motor 113 of the dispensing assembly 112a such that the reservoirs 108a selectively rotate on or about the dispensing assembly 112a. In other embodiments, the dispensing assembly 112a can selectively rotate about the reservoirs 108a.

The medication reservoirs 108a of the reservoir assembly 106a can each include or define medication pods 140. The reservoirs 108a are sized and shaped to hold one or more, capsules, pills, tablets, and the like. With certain applications, the reservoirs 108a can be sized and shaped to contain a single standardized pod that contains medication in a solid, liquid or powder form. The pods 140 can be prefilled with medication and provided to the patient with the reservoir assembly 106a. In various embodiments, the pods 140 are not separable from and are integrated with, or part of, the reservoirs 108a.

The pods 140 can include a funneling portion 144. Spinning rotation of the assembly 106a correspondingly aligns a reservoir 108a and a corresponding bottom outlet 108b with a top inlet 150 of the dispensing assembly 112a. As such, medication, such as one or more pills P, capsules, and the like, can drop or otherwise travel from the medication pod 140, through the bottom outlet 108b of the reservoir assembly 106a, and into the top inlet 150 of the dispensing assembly 112a, for dispensing through the dispenser 122. The assemblies 106a, 112a are adapted to snap or otherwise couple together such that the reservoir assembly 106a rotates relative to the dispensing assembly 112a. Further, the reservoir assembly 106a, or portions thereof, can be disposable in various embodiments and can be preloaded with customized drug regimens, including over-encapsulated medication, and delivered to the patient for use with the system 100.

The bottom of each of the reservoirs 108a (e.g., at outlet 108b) can include a bar-code, electromagnetic code, or other identifying indicia or elements, and the dispensing assembly 112a can include a sensor, reader mechanism or device, etc. to read or sense the unique signature or identification characteristic of the individual reservoirs 108a. When the dispensing assembly 112 reads or detects the unique signature for the reservoir 108a containing the correct or desired medication, the reservoir assembly 106a is rotated into position for dispensing from that reservoir 108a. Dispensing of the medication is detected and stored. Further, dispensing data, such as the time and date the medication was dispensed, is processed and stored at the system 100 or via the cloud system. In addition, data from peripheral devices, inputted answers from the patient, and other data and information can be processed and stored as well, as detailed further herein.

The bottom outlet 108b, or another portion of the assemblies 106a, 112a, can include a rotating output element 146. In certain embodiments, the rotating output element 146 can be provided with or connected to the upper assembly 106a (e.g., within the outlet 108b) such that the element 146 is above the cavity opening 150 upon registered rotation. Further, a pill P falling or otherwise traveling out of the element 146 and down through opening 151 can enter an additional or secondary rotating element 146. Such an embodiment with dual rotating elements 146 can increase the level of redundancy and safety provided, and can facilitate medication confirmation with the lower assembly 112a permitting bar code reading, or implementing other identification devices or techniques.

The rotating element 146 can include a cavity opening 151. In use, as shown in FIGS. 10-11, pills P, or other medication types or medication delivery vessels, travel through the funneling portion 144 of the pod 140 and into the rotating element 146. The cavity opening 151 defined in the rotating element 140 can receive a single pill P, multiple pills P, or other forms of medication. Upon rotation of the element 146—e.g., triggered by spinning of the reservoir assembly 106a or other mechanisms—the medication falls or otherwise exits the opening 151 of the rotating element 146 and drops into the dispensing assembly 112a (e.g., through opening 150), as depicted in FIG. 11. The opening 150 is in fluid communication with the dispenser 122 such that the medication can traverse to and through the dispenser 122 and out to the user—e.g., received into the cup 124. Again, detection, processing, and storage of this dispensing data is facilitated by the processor 105a.

The compact (e.g., cylindrical) medication dispenser system 100 of various embodiments can employ software algorithms, blood pressure measurements, and symptom assessments to determine the best blood pressure medication for an individual patient, for example. The system 100 can be prescribed by clinicians and can arrive prefilled with multiple types and dosages of medications. The system dispenses short courses of specific drugs and dosages while collecting blood pressure and symptom measurements. Treatments are compared systematically to determine which is most effective and least bothersome to the patient. The optimal drug is then continually dispensed while compliance and ongoing treatment effect are monitored.

Various embodiments of the system 100, including but not limited to those of FIGS. 8-11, can be used to treat high blood pressure and other specific medical conditions. The base or dispensing assembly 112a can include the computing processor 105a and connectivity hardware (e.g., Bluetooth, Wi-Fi, ethernet, USB, etc.) and can pair and communicate with other computing devices 103, such as mobile devices (e.g., smartphones, tablets, etc.), desktop computers, and other devices and peripherals, such as blood pressure cuffs, weight scales, wearables, etc. The processor 105a is operatively connected and in communication with the one or both of the assemblies 106a, 112a, and the components, mechanisms, and devices thereof, such that the processor 105a can control the spinning upper disc 106a and track each mechanical step in the capsule or medication dispensing process. The processor 105a can be controlled by software that contains detailed blood pressure treatment algorithms that enable ongoing patient assessment and medication adjustments. Accordingly, the software and connectivity of the system 100 enable ongoing data exchange with clinicians. New reservoir assemblies 106a can be sent to the user patient for coupling to the system 100 with new medications, new medication dosages, and the like. The monitoring and tracking of the system 100 and its software and processor 105a provide accurate, responsive, and customizable medication treatment regimens.

Figure 12:
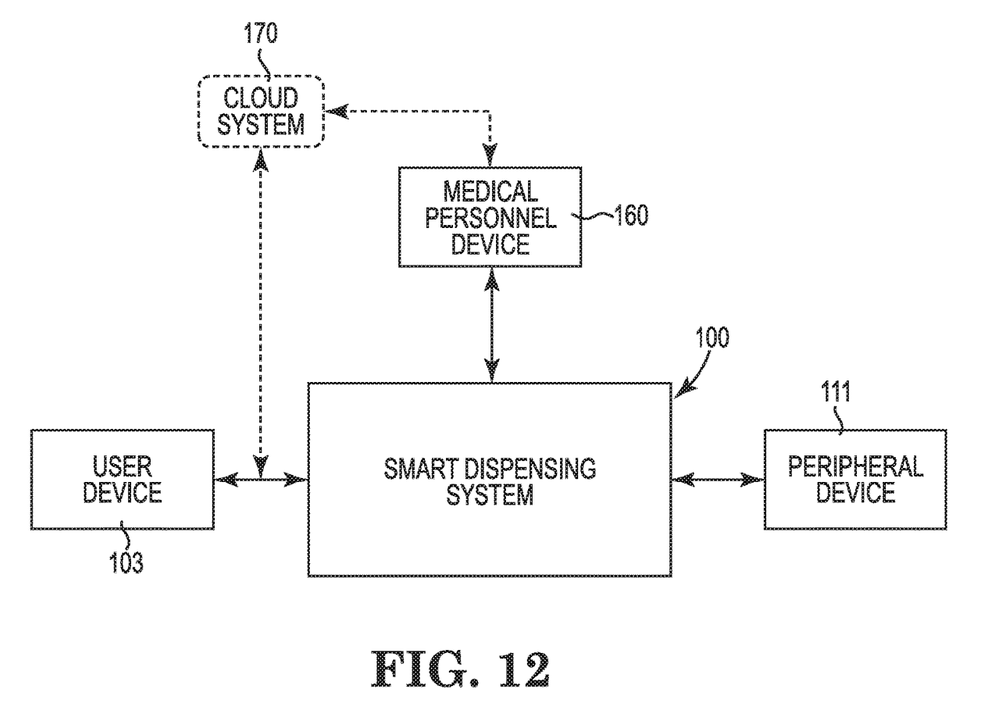
FIG. 12 is a diagram of a hardware and device communication architecture for use with, and including, a medication dispensing system, in accordance with embodiments of the present invention.
Figure 13:
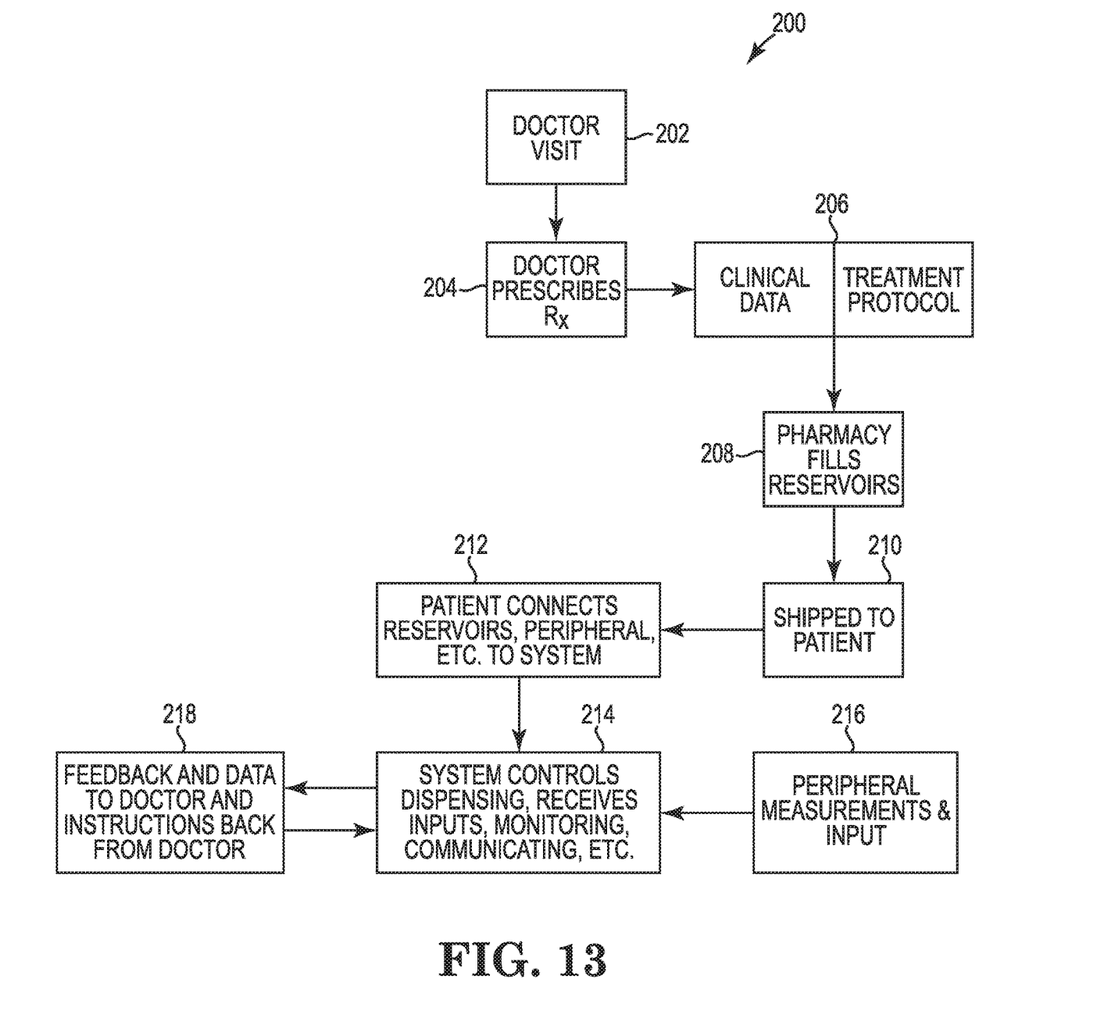
FIG. 13 is a flow diagram showing an exemplary method of use and operation for a medication dispensing system, in accordance with embodiments of the present invention.

Referring to FIGS. 12-13, embodiments of the architecture and dispensing methodology for the system 100 are provided. These communication, interaction, and treatment processes and elements can be applied to or incorporated with, in whole or in part, any of the embodiments, aspects, components, devices, and methods of the present invention.

The exemplary architecture of FIG. 12 provides for operative communication between the dispensing system 100 and the user devices 103, the peripheral devices 111, and the medical personnel devices 160 (e.g., physician or clinician devices). In addition, various embodiments can include a cloud computing system 170. The cloud system 170 can provide portal access for medical personnel, patients, pharmacies, etc., as well as facilitate and control dispensing, data storage, treatment processing, and communication between the medical device 160, the user device 102, and the system 100, as described herein.

As detailed herein, the system 100 is an interactive tool that connects a doctor in a clinic (e.g., at medical computing device 160) with a patient in their home, can interact with peripheral devices 111, can process data, prompt, and receive input at user devices 103. The system can use ethernet, Wi-Fi, cellular, or any other form of wired or wireless connectivity to receive instructions, directly or indirectly, from the medical personnel device 160. If Internet connectivity is not available, there is one or more USB ports (or other data transfer and communication ports) that facilitates the delivery of instructions—e.g., by a thumb drive, a computing device, or similar storage or data communication devices.

The peripheral devices 111 can include weight scales, blood pressure monitoring devices or cuffs, wearables like a Fitbit or an Apple Watch, and a myriad of other health, measurement, and monitoring devices. In certain embodiments, communication with these distinct devices 111 and systems can be accomplished via Bluetooth connectivity. This allows input of patient measurements and data which are then transmitted to the clinic or other medical personnel for review and processing—and communication back from the medical personnel to the system 100.

The system 100 also tracks medication compliance and records the effect of treatment. Each time a medication is dispensed, the medication name, dose, and time of day are processed and stored in a log or database. Periodically, the device 103 or the system 100 itself can prompt the patient to answer, via inputs, a symptom questionnaire or to make a physiologic measurement. For example, blood pressure or weight data can be received from the operatively coupled peripheral device 111, or from manually inputted data and information. The results are transmitted and stored in a database log—e.g., at the user device 103, the controller 105, the medical personnel device 160, and/or the cloud system 170.

The user device 103 allows the patient to receive prompts and messages from the system 100, while also permitting the patient to input data and otherwise interact with the system 100. User devices 103 can include mobile devices such as smart phones and tablet devices, laptops, personal computers, or any other computing device capable of communicating with the system 100 (e.g., via wired or wireless connectivity).

The clinician or medical personnel device 160 can be in operative communication with the system 100 and the user device 103. The clinician devices 160 can include mobile devices such as smart phones and tablet devices, laptops, personal computers, or any other computing device capable of communicating with the system 100 (e.g., via wired or wireless connectivity). Further, the clinician devices 160, and the user devices 103, can communicate with and process data and execute software code through or via the network computing system 170, such as a cloud server, in certain embodiments of the system 100.

Further, the body 101, or other assemblies and sections of the system 100, can include an LCD or like display that displays text and images and facilitates touchscreen inputs. A speaker output device can be included to allow for the transmission of audible information to the patient.

FIG. 13 provides a flow diagram of a process of using the system 100 in accordance with embodiments of the present invention. For illustrative purposes, this exemplary process will be directed to the evaluation and treatment of high blood pressure. However, this process is not meant to be limiting and the various process steps and integration and use of the system 100 can be applied to any other medical condition and treatment that requires a patient to take medication, including prescription medication. First, at step 202, the user patient visits their doctor (or other medical personnel). At that time, it is discovered that the patient has an elevated blood pressure reading. The doctor then prescribes a blood pressure medication (step 204) via the clinic's electronic medical record system ("EMR"), which is in operative communication via a web portal or other interface with the cloud system 170. The doctor can enter various clinical and treatment protocol data at step 206. The protocol options will be consistent with the clinical data entered and will include a recommended protocol. In addition, the doctor can choose from other customized treatment protocols. Once the treatment protocol is chosen or inputted, a pharmacy (such as a compounding pharmacy) will be instructed to fill the reservoirs of the reservoir assembly 106a of the system 100 with the prescribed medication consistent with the treatment protocol. Again, the pharmacy personnel can be in operative communication with the cloud system 170 and the doctor to receive, process, and disseminate information and data. At step 208, the pharmacy fills the reservoirs 108a of the reservoir assembly 106a with the prescribed medication. The reservoir assembly 106a can be a separate section of the overall dispensing system 100 with such embodiments, e.g., a disc-shaped component. The filled reservoir assembly disc 106a is then shipped to the patient at step 208. If this is the initial treatment for the patient, the base dispensing assembly 112a can also be shipped to the patient and include operation and use instructions, e.g., how to connect the system 100 to the cloud system 170 via a wireless or wired connection. One or more peripheral devices 111, such as a blood pressure cuff, can be provided as well with the system 100 at this initial shipment stage. If this is not the initial stage for the patient, the shipment can simply include the filled and disposable reservoir assembly disc 106a.

The reservoir assembly disc 106a can be filled with enough medication to run a treatment protocol for a fixed period of time—e.g., up to three months. All of the reservoirs 108a in the reservoir assembly disc 106a can be filled with medication, or one or more of the reservoirs 108a can be left empty. The treatment protocol and the corresponding duration for that protocol will be the determining factors. In one prescribed treatment example, the reservoir assembly disc 106a is filled for a one-month run, and only two or three reservoirs 108a include blood pressure medication or a placebo (depending on the protocol). The other reservoirs 108a (e.g., six or seven reservoirs) can be filled with the patient's other prescribed medications, such as medications for cholesterol, reflux, diabetes, etc. This inclusion of multiple distinct medications within the reservoir assembly disc 106a is facilitated by the doctor. The doctor, via the cloud system 170, can have the patient's other medication prescriptions transferred to the subject pharmacy. Accordingly, a new reservoir assembly disc 106a can be shipped to the patient every month, filled with the appropriate medication from the treatment protocol as well as refills of the patient's other medications. It is noted that the cloud system 170 and/or the personnel and company controlling and facilitating the processes described herein, can act as the pharmacy for filling and distribution of the reservoirs discs 106a and can monitor, process, and control each aspect of the processes after the initial doctor visit and prescription steps.

At step 212, if this is the initial shipment and receipt of the system 100, the patient will set up the system, components, and any peripherals 111. If the patient already has at least the base dispensing section 112a of the system 100, the patient simply connects the reservoir assembly disc 106a to the dispensing section 112a for use. The patient then begins the prescribed treatment protocol through the system 100 at step 214. The system 100 receives inputs and data, controls dispensing, monitors adherence, and can provide notifications and operatively communicate data and feedback to the user device 103 as well as the cloud system 170 and the medical personnel device 160 (step 218).

In those example situations where a diagnosis of hypertension is in doubt, the treatment protocol may begin with a placebo and blood pressure measurements inputted from the peripheral device 111 for two weeks to confirm the diagnosis. Otherwise, medications will be dispensed from the system 100 each day while the patient measures their blood pressure via the peripheral device 111. The patient can also input answers to a series of symptom questions at the device 103 or directly at the system 100—e.g., via a touch input device provided with the base dispensing assembly 112a. If blood pressure readings do not reach goal after an allotted time, or side effects develop, the system 100 per the protocol in place will automatically change the dose or the medication itself. The treatment change will be seamless and does not require further inputs from the patient or their doctor. The system 100 will send notification of the change in treatment and the reason for the change (e.g., poor response or side effect) to the patient's doctor. Also, when medication refills are due, the system 100 will provide the pharmacy with up-to-date details of the medications dispensed and the progression of the protocol. This will allow the pharmacy to adapt to the patient's unique spot in the protocol and, accordingly, fill and ship a new reservoir assembly disc 106a that contains the medications and dosages that are required or might be required as the treatment protocol continues. The patient will then receive the disc 106a and connect it to the base dispensing assembly 112 for another period (e.g., one month) of ongoing use. Again, the treatment of high blood pressure is provided for illustrative purposes only and is not intended to limit the various treatment protocols, medications, applications, or uses for the system 100.

Figure 14:
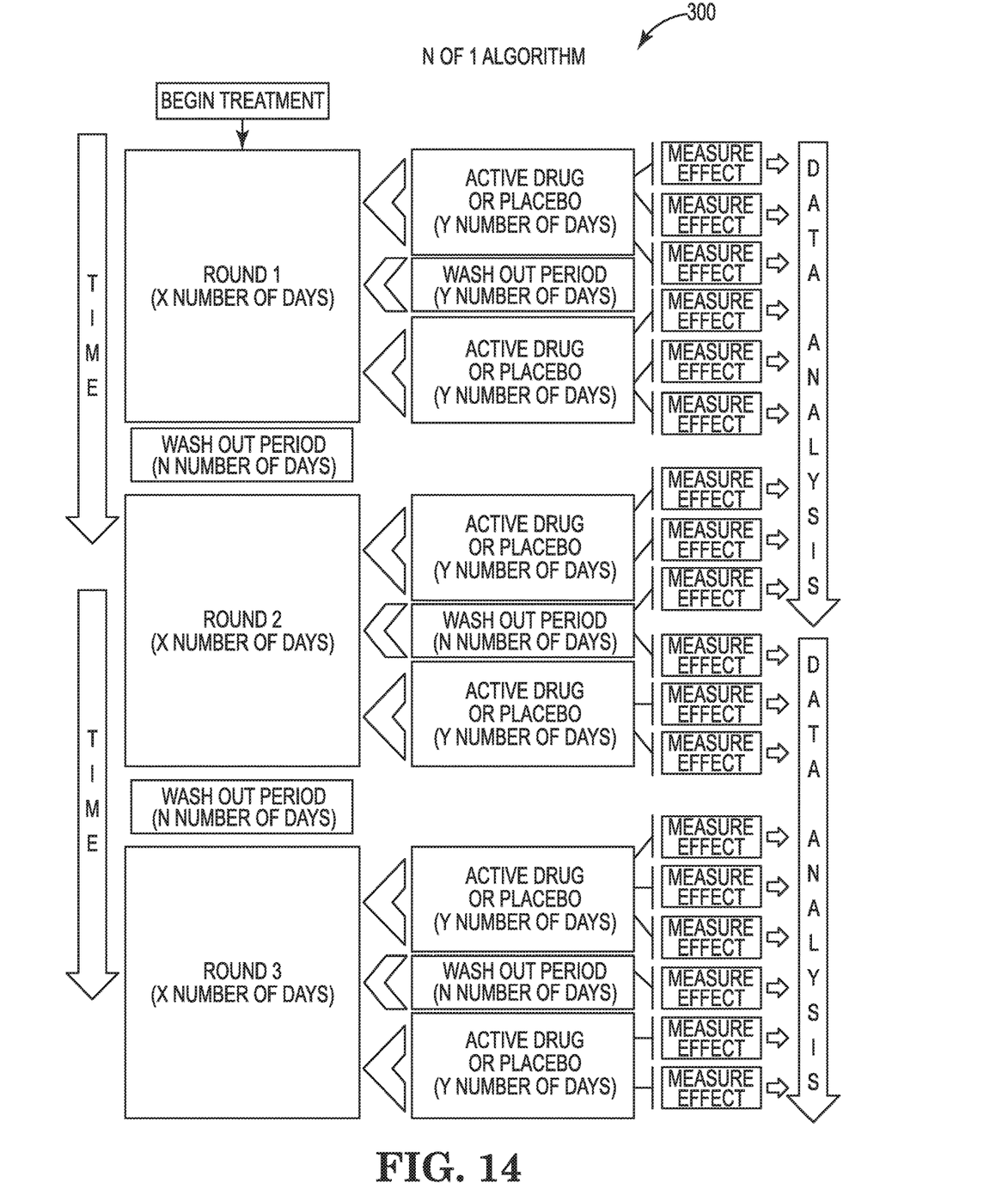
FIG. 14 is a diagram for N-of-1 trial processing, in accordance with embodiments of the present invention.

Referring to FIG. 14, an embodiment of system software 300 translates the clinician's treatment plan into the precise delivery of care in the patient's home or other location. This may be as basic as ensuring the correct medication and dose is delivered at the optimal time—and reminding the patient of diet and physical activity goals for the day—or it can be more complex by including implementation of different treatment protocols, including N-of-1 trials and sequential monotherapy. The software 300 can be executed with the processor 105a of the system 100 itself, at the cloud system 170, or at the user device 103.

The software 300 also performs ongoing statistical analysis of data inputs from the patient. For example, as an N-of-1 trial proceeds, the ongoing comparisons between treatments will lead to updates of the likelihood that, in the end, there will be statistical and meaningful differences between treatments. Substantive differences between treatments will make it much more likely that an eventual difference will be found.

Figure 15:
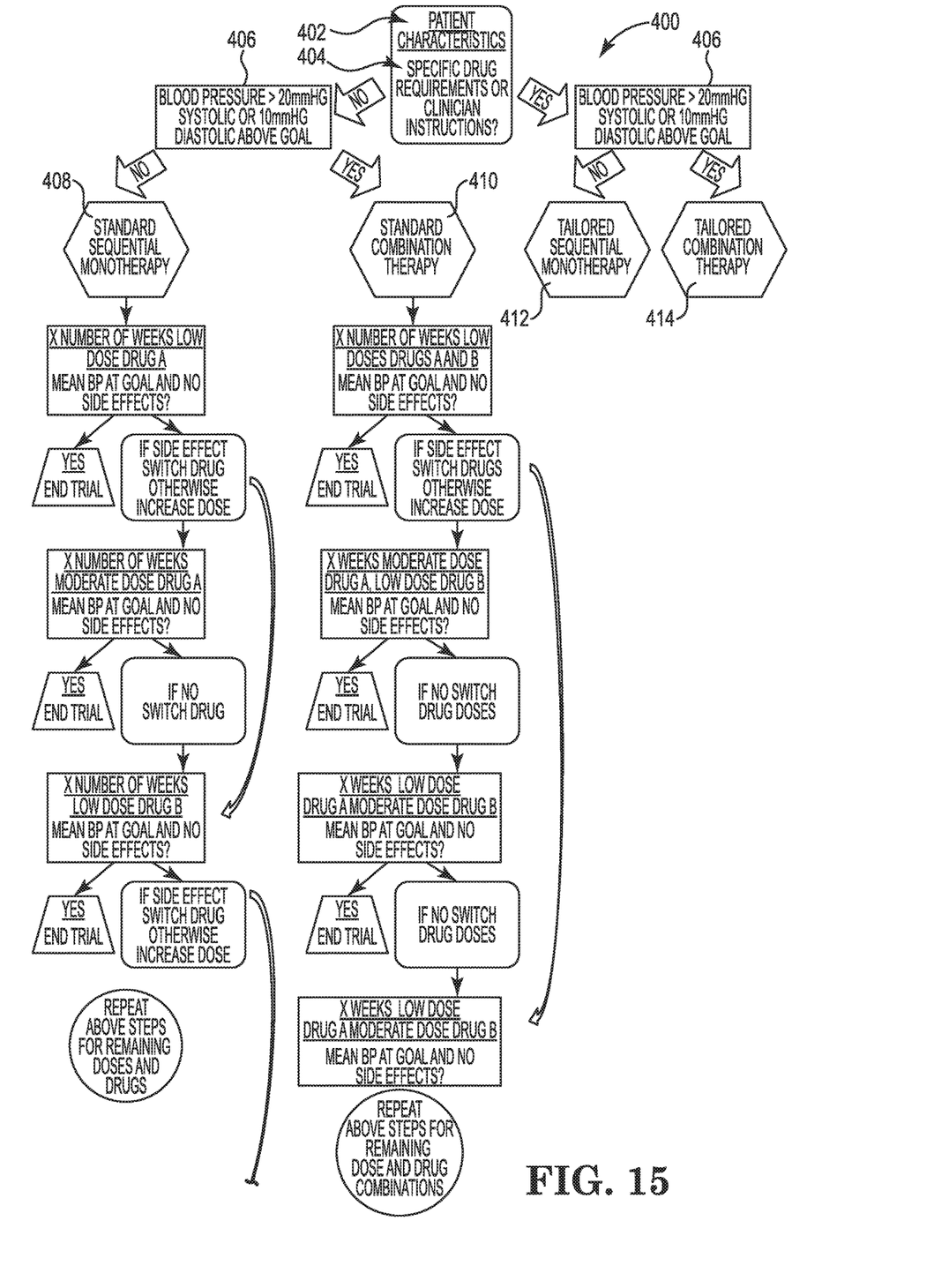
FIG. 15 is a flow diagram of the processing methods for a medication dispensing system, for the treatment of hypertension and other specific conditions, in accordance with embodiments of the present invention.

Referring to FIG. 15, embodiments of the system 100 can include pre-filled reservoirs with over-encapsulated medications loaded therein—e.g., at a remote or separate location, prior to delivery to a patient. The medications can be dispensed from the device by rotating the reservoirs, or from each reservoir position absent rotation. This embodiment can include the method and software 400 adapted to treat specific conditions—e.g., hypertension and a myriad of other medical conditions or issues.

The software and methods 400 will enable medications to be dispensed in a manner that personalizes and optimizes the treatment (such as hypertension) according to the consensus recommendations of accepted experts, boards, and panels, such as the American College of Cardiology (ACC), the American Heart Association (AHA), etc. In addition to N-of-1 protocols, the algorithms and processing of the software 400 can include sequential monotherapy, stepwise dose adjustment patterns, and other treatment protocols and techniques.

As illustrated in the flow chart of FIG. 15, the method and software 400 of the system 100 provides treatment protocols consistent with recommendations and published methodology—again, provided by the ACC, AHA, and the like. At step 402, patient characteristics can be entered on-line, or on-site, by a clinician or a patient via the secured website or portal of the cloud system 170. A questionnaire can be provided to received pertinent information entered. For instance, pertinent medical history can be obtained, including any history of relevant conditions, past issues, heart failure, kidney disease, myocardial infarctions, atrial fibrillations, proteinuria, prostatic hyperplasia, hyperthyroidism, angioedema bronchospasm, asthma, pregnancy, heart blocks, gout, hyperkalemia, hyponatremia, hypercalcemia, renovascular disease, etc. This is partial list intended as an example of history that will be obtained and is not intended to be exhaustive or limiting. Also, a complete list of allergies, including history of ace inhibitor related cough, and similar data, can be obtained.

At step 404, the patient characteristics will, in some cases, result in specific drug treatment requirements. Some conditions or medical histories will indicate that a certain drug be used or avoided. Also, the online portal will allow a patient's clinician to specify a strong treatment preference. For example, a clinician, for various reasons, may believe a certain blood pressure medication would be beneficial. If there is a specific drug requirement or strong clinician preference, a tailored treatment protocol can be used. Otherwise the process will proceed with a standard treatment protocol.

At step 406, information entered or inputted into the software 400 (e.g., online) can include baseline blood pressure measurements. If blood pressure is greater than 20 mmHg systolic or 10 mmHG diastolic above goal, treatment will begin with combination therapy, for example.

As illustrated with step 408, standard therapy utilizes the drugs shown to reduce clinical events. Consistent with the best clinical evidence to date and according to the recommendations of the ACC/AHA, the primary agents used in the treatment of hypertension include thiazide diuretics, ACE inhibitors, angiotensin receptor blockers (ARBs), and calcium channel blockers (CCBs). These drugs are used in the treatment protocols delivered by the system 100 (both standard and tailored protocols). In the initial standard and tailored protocols, low and moderate doses of each drug will be available. In the resistant hypertension protocols, high doses of these drugs will be available.

Referring to step 410, combination therapy will utilize all combinations of the four drug classes noted above, except ACE inhibitors and ARBs should not be combined. Also, the underlying treatment principle is to use the lowest doses of medications needed to reach a blood pressure goal. This approach minimizes the risk of side effects as they become more likely as the doses of medication increase. Thus, the combination of two moderate doses is not used until all low/low and low/moderate combinations have been tried.

Referring to step 412 and 414, tailored protocols can be the same as standard protocols, except certain drugs will be removed from the treatment algorithm if contraindicated. Also, certain drugs may be moved to the beginning of the algorithm if preferred, or to the back of the algorithm if the preference is to avoid their use if possible.

Aspects of the software code of the invention, or code used with the invention, can take the form of a plugin or app, a web app, or a website interface, and can interface with various protocols or software using APIs or other means of interacting with computing software and systems.

Various computing devices or systems 100, 103, 160 described herein can be included and adapted to process and carry out the aspects, computations, and algorithmic processing of the system 100 of the present invention. Computing systems and devices of the present invention may include a computing processor, which may include one or more microprocessors and/or one or more circuits, such as an application specific integrated circuit (ASIC), field-programmable gate arrays (FPGAs), etc. Further, the computing system and devices can include a network interface. The network interface is configured to enable communication with the network, other devices and systems, and servers, using a wired and/or wireless connection.

The devices or computing systems may include memory, such as non-transitive memory, which may include one or more non-volatile storage devices and/or one or more volatile storage devices (e.g., random access memory (RAM)). In instances where the devices include a processor, computer readable program code may be stored in a computer readable medium or memory, such as, but not limited to storage media (e.g., a hard disk or solid-state drive), optical media, memory devices (e.g., random access memory, flash memory), etc. The computer program or software code can be stored on a tangible, or non-transitive, machine-readable medium or memory. In some embodiments, computer readable program code is configured such that when executed by a processor, the code causes the device to perform the steps described above and herein. In other embodiments, the device is configured to perform steps described herein without the need for code.

It will be recognized by one skilled in the art that these operations, algorithms, logic, method steps, routines, sub-routines, and modules may be implemented in software, in firmware, in special purpose digital logic, and any combination thereof without deviating from the spirit and scope of the present invention as recited within the claims attached hereto.

Server processing systems, such as those included with the cloud computing system 170, for use or connected with the system 100, devices, and components of the present invention, can include one or more processors, and/or one or more circuits, such as an application specific integrated circuit (ASIC), field-programmable gate arrays (FPGAs), etc. A network interface can be configured to enable communication with the network, using a wired and/or wireless connection, including communication with the devices or computing systems and devices 100, 103, 160 disclosed herein. Memory can include one or more non-volatile storage devices and/or one or more volatile storage devices (e.g., random access memory (RAM)). In instances where the server system includes a processor, computer readable program code may be stored in a computer readable medium, such as, but not limited to storage media (e.g., a hard disk or solid-state drive), optical media, memory devices, etc.

Aspects of the present invention can be embodied as software code residing on the user's computing device 103 (e.g., desktop, tablet, mobile, and the like) and/or on one or more server systems 170. The various received or processed data of the present invention can be included on and transferred to and from a storage area network (SAN), a data cloud, or any computing device for storing the file or files being uploaded, downloaded, or processed.

While the methods, steps, and processing described above and illustrated in the drawings are shown as a sequence of steps, this was done solely for the sake of illustration. Accordingly, it is contemplated that some steps may be added, some steps may be omitted, the order of steps may be re-arranged, and some steps may be performed in parallel.

For purposes of interpreting the claims for the present invention, it is expressly intended that the provisions of 35 U.S.C. § 112(f) are not to be invoked unless the specific terms "means for" or "step for" are recited in a claim.

While the invention has been described in connection with what is presently considered to be the most practical and preferred embodiments, it will be apparent to those of ordinary skill in the art that the invention is not to be limited to the disclosed embodiments. It will be readily apparent to those of ordinary skill in the art that many modifications and equivalent arrangements can be made thereof without departing from the spirit and scope of the present disclosure, such scope to be accorded the broadest interpretation of the appended claims so as to encompass all equivalent structures and products. Moreover, features or aspects of various example embodiments may be mixed and matched (even if such combination is not explicitly described herein) without departing from the scope of the invention.

What is claimed is:

1. A smart medication dispensing system, comprising:
a) a housing including an upper portion and a lower portion;
b) a medication reservoir assembly within the upper portion of the housing, the reservoir assembly including a plurality of medication reservoirs extending through the assembly to define a plurality of bottom outlets, wherein each bottom outlet includes an identifier for uniquely identifying the medication reservoir associated therewith and each medication reservoir is configured to receive medication of a specific type and a specific dose;
c) a medication dispensing assembly within the lower portion of the housing, the dispensing assembly including:
 i. a top inlet alignable with at least one bottom outlet of the plurality of bottom outlets;
 ii. a sensor for reading the identifiers on the plurality of bottom outlets, the identifiers including information on the specific type and the specific dose of medication associated with the plurality of medication reservoirs; and
 iii. a dispenser for receiving medication from the top inlet and dispensing medication to a user through an output of the dispensing assembly;
d) a central drive within the housing for rotating the reservoir assembly relative to the dispensing assembly about a central vertical axis;
e) a touch screen input device attached to an exterior portion of the housing and configured to send, receive, and display information related to dispensing and monitoring operations;
f) at least one user computing device configured to send and receive data from the system via wired or wireless connectivity;
g) an array of communication devices for connecting one or more peripheral devices to the system, the one or more peripheral devices including at least one of blood pressure monitors, heartbeat monitors, weight scales, and other personal health monitoring devices; and
h) a controller for controlling medication dispensing operations, the controller including a processor and a memory having processor-executable instructions thereon to cause the processor to:
 i. receive a medication protocol with instructions for dispensing medication of a specific type in a specific dose at a specific time;
 ii. rotate the reservoir assembly into position for dispensing a desired medication from a reservoir upon reading the identifier of a reservoir containing the desired medication;
 iii. dispense the desired medication from the reservoir assembly into the dispensing assembly and through the output of the dispensing assembly to a user;
 iv. receive biometric data on the user acquired from at least one of the touch screen input device, the at least one user computing device, and the one or more peripheral devices;
 v. personalize a medication protocol based in part on the biometric data used to measure the effect of the medication on a user; and
 vi. send an alert or notification on the effect of the medication protocol to one or more users for review and processing.

2. The smart medication control, dispensing and monitoring system of claim 1, further comprising each reservoir having a horizontally rotating element at the bottom outlet, the rotating element having a cavity and a cavity opening to receive the medication from within the reservoir and thereafter rotating approximately 180° to drop the medication therefrom.

3. The smart medication control, dispensing and monitoring system of claim 2, further comprising a second horizontally rotating element below the top inlet, the second rotating element having a cavity and a cavity opening to receive the medication from one of the first rotating elements within the reservoir and thereafter rotating approximately 180° to drop the medication therefrom into the dispenser.

4. The medication control, dispensing and monitoring system of claim 1, wherein the central drive rotates the horizontally rotating element.

5. The smart medication control, dispensing and monitoring system of claim 1, wherein the housing with the upper portion has a removable lid, the housing and the lid not being transparent so as to hide the pharmacy deliverable reservoir assembly and the medications therein.

6. The medication control, dispensing and monitoring system of claim 1, wherein the user device facilitates the user to respond to a series of symptom questions.

7. The medication control, dispensing and monitoring system of claim 1, wherein the touch input device facilitates the user to respond to a series of symptom questions.

8. The medication control, dispensing and monitoring system of claim 1, wherein the user devices comprise at least one of a smart phone, a tablet computer, a laptop computer or a desk top computer.

9. The smart medication control, dispensing and monitoring system of claim 1, further comprising one or more output devices including at least one of a screen display or a speaker.

10. The smart medication control, dispensing and monitoring system of claim 1, wherein the medication for the system is over-encapsulated.

11. The smart medication control, dispensing and monitoring system of claim 1, wherein the medication reservoir assembly is separable and insertable within the upper portion of the housing.

12. The smart medication control, dispensing and monitoring system of claim 1, wherein each medication reservoir is configured to receive a single medication pod containing medication of a specific type and a specific dose.

13. The smart medication control, dispensing and monitoring system of claim 1, wherein the system is capable of conducting N-of-1 drug trials.

14. The smart medication control, dispensing and monitoring system of claim 1, further comprising a second sensor for detecting one of the medications being dispensed.

* * * * *